US012642477B2

(12) United States Patent
Karjalainen et al.

(10) Patent No.: US 12,642,477 B2
(45) Date of Patent: Jun. 2, 2026

(54) ELECTRODE PATCH, SYSTEM, AND METHOD FOR DETECTING INDICATOR OF PARKINSON'S DISEASE IN PERSON

(71) Applicant: Adamant Health Oy, Helsinki (FI)

(72) Inventors: Pasi Karjalainen, Kuopio (FI); Saara Rissanen, Kuopio (FI)

(73) Assignee: Adamant Health Oy, Helsinki (FI)

( * ) Notice: Subject to any disclaimer, the term of this patent is extended or adjusted under 35 U.S.C. 154(b) by 686 days.

(21) Appl. No.: 16/975,453

(22) PCT Filed: Feb. 28, 2019

(86) PCT No.: PCT/EP2019/055002
§ 371 (c)(1),
(2) Date: Aug. 25, 2020

(87) PCT Pub. No.: WO2019/166557
PCT Pub. Date: Sep. 6, 2019

(65) Prior Publication Data
US 2021/0015419 A1     Jan. 21, 2021

(30) Foreign Application Priority Data

Mar. 1, 2018     (EP) ..................................... 18159445

(51) Int. Cl.
*A61B 5/00*        (2006.01)
*A61B 5/296*       (2021.01)
*A61B 5/389*       (2021.01)
(52) U.S. Cl.
CPC ............ *A61B 5/4082* (2013.01); *A61B 5/296* (2021.01); *A61B 5/389* (2021.01); *A61B 5/6833* (2013.01);

(Continued)

(58) Field of Classification Search
CPC ......... A61B 5/4082; A61B 5/40; A61B 5/296; A61B 5/6833; A61B 5/389
See application file for complete search history.

(56) References Cited

U.S. PATENT DOCUMENTS

| | | | |
|---|---|---|---|
| 6,032,065 A | 2/2000 | Brown | |
| 2003/0109905 A1* | 6/2003 | Mok | ........................ A61N 1/04 607/60 |

(Continued)

FOREIGN PATENT DOCUMENTS

| | | |
|---|---|---|
| CN | 106 805 969 A | 6/2017 |
| CN | 107 622 260 A | 1/2018 |

(Continued)

OTHER PUBLICATIONS

Rissanen at al., "Surface EMG and acceleration signals in Parkinson's disease: Feature extraction and cluster analysis" Medical & Biological Engineering & Computing, Sep. 2008, vol. 46, pp. 849-858. (Year: 2008).*

(Continued)

*Primary Examiner* — Matthew Kremer
(74) *Attorney, Agent, or Firm* — Ziegler IP Law Group, LLC.

(57)     ABSTRACT

The present disclosure describes an electrode patch, and a method, a measurement arrangement, and a detection system utilizing the electrode patch for detecting an indicator of Parkinson's disease in a person from a muscle in a limb of the person. The electrode patch comprises two measurement electrodes, wherein a distance between centres of the measurement electrodes is above 2 cm and less than 4 cm, and a reference electrode positioned such that a lateral distance of from a centre of the reference electrode from to an axis passing through the centres of the measurement electrodes is at least he distance between the measurement electrodes.

16 Claims, 3 Drawing Sheets

(52) U.S. Cl.

CPC . *A61B 2562/0219* (2013.01); *A61B 2562/164* (2013.01)

(56) References Cited

U.S. PATENT DOCUMENTS

| | | | | |
|---|---|---|---|---|
| 2003/0125636 A1* | 7/2003 | Jeong | .................. | A61B 5/7415 |
| | | | | 600/546 |
| 2005/0240086 A1 | 10/2005 | Akay | | |
| 2010/0280579 A1* | 11/2010 | Denison | ................. | G16H 50/30 |
| | | | | 607/62 |
| 2012/0150047 A1* | 6/2012 | Terumoto | ........... | A61B 5/02427 |
| | | | | 600/479 |
| 2014/0194790 A1* | 7/2014 | Crunick | ................. | A61H 23/02 |
| | | | | 601/48 |
| 2014/0200920 A1* | 7/2014 | Malec | .................... | G06Q 10/10 |
| | | | | 705/3 |
| 2015/0106020 A1* | 4/2015 | Chung | .................. | G16H 40/67 |
| | | | | 702/19 |
| 2015/0272483 A1 | 10/2015 | Etemad | | |
| 2016/0262685 A1 | 9/2016 | Wagner | | |
| 2017/0360329 A1* | 12/2017 | Derkx | .................... | A61B 5/389 |

FOREIGN PATENT DOCUMENTS

| | | | | | | |
|---|---|---|---|---|---|---|
| JP | 2015534856 A | * | 12/2015 | .......... | A61B 5/0036 |
| JP | 2016-532468 A | | 10/2016 | | |
| WO | WO 2009/134246 A1 | | 11/2009 | | |
| WO | WO 2016/149832 A1 | | 11/2009 | | |
| WO | WO 2012/167177 A1 | | 12/2012 | | |
| WO | WO2016/067101 | | 5/2016 | | |
| WO | WO2016149832 | * | 9/2016 | .......... | A61B 5/0531 |
| WO | WO2017201538 | * | 11/2017 | ....... | A61B 2562/046 |

OTHER PUBLICATIONS

"Scalar." Merriam-Webster.com Dictionary, Merriam-Webster, https://www.merriam-webster.com/dictionary/scalar. Accessed Jun. 24, 2025. (Year: 2025).*

English machine translation of JP 2015-534856, Clarivate Analytics, 61 pages, printed on Jun. 24, 2025 (Year: 2025).*

Rissanen, Saara et al., "Analysis of Dynamic Voluntary Muscle Contractions in Parkinson's Disease," IEEE transactions on biomedical engineering—Jul. 2009, 10 pages (Year: 2009).*

International Search Report issued in International Application No. PCT/EP2019/055002, mailed Jun. 4, 2019.

Written Opinion of the International Searching Authority issued in International Application No. PCT/EP2019/055002, mailed Jun. 4, 2019.

Summons to attend oral proceedings pursuant to Rule 115(1) EPC issued in counterpart EP Application No. 18 159 445.8, mailed Sep. 21, 2023.

Hermie J Hermens et al: "Development of recommendations for SEMG sensors and sensor placement procedures", Journal of Electromyography and Kinesiology, vol. 10, No. 5, Oct. 1, 2000 (Oct. 1, 2000), pp. 361-374, XP035110773, ISSN: 1050-6411, DOI: 10.1016/S1050-6411(00)00027-4.

Saara M.Rissanen et al., Analysis of EMG and Acceleration Signals for Quantifying the Effects of Deep Brain Stimulation in Parkinson's Disease, IEEE Transactions on Biomedical Engineering, vol. 58, No. 9, Jan. 13, 2011, pp. 1-21.

Alexander Y.Meigal et al. Non-linear EMG parameters for differential and early diagnostics of Parkinson's disease, Frontiers in Neurology, vol. 4, No. 135, Sep. 17, pp. 1-8.

Office Action issued in counterpart Japanese Application No. 2020-545120, mailed Dec. 21, 2023 with English language translation thereof.

Office Action issued in counterpart Japanese Application No. 2020-545120, mailed Aug. 31, 2023 with English language translation thereof.

Office Action issued in counterpart Australian Application No. 2019226356, mailed Feb. 2, 2024.

* cited by examiner

ELECTRODE PATCH, SYSTEM, AND METHOD FOR DETECTING INDICATOR OF PARKINSON'S DISEASE IN PERSON

CROSS REFERENCE TO RELATED APPLICATIONS

The present application is a § 371 National Phase application based on PCT/EP2019/055002, filed on Feb. 28, 2019, which claims the benefit of European application No. 18159445.8 filed Mar. 1, 2018, the subject matter of each of which is incorporated by reference in their entirety.

FIELD

The invention relates to measurement and analysis of biosignals, and in particular, to a method for detecting at least one indicator of Parkinson's disease (PD) in biosignals measured from a person.

BACKGROUND INFORMATION

Parkinson's disease (PD) is a long-term degenerative disorder of the central nervous system that mainly affects the motor system. The symptoms generally come on slowly over time. As the disease progresses, the symptoms become more and more unpredictable. There is no accurate data analysis about the symptoms. It is difficult to form a comprehensive view of the time varying symptoms and to find a correct drug and its dosage, and the scheduling of doses, particular in cases where the disease has already progressed to later stages. It may also be difficult to adjust deep brain stimulation (DBS) settings, and to choose optimal treatment method in each situation.

BRIEF DISCLOSURE

An object of the present disclosure is to provide a method and an apparatus for implementing the method so as to alleviate the above disadvantages. The object of the disclosure is achieved by a method and an arrangement that are characterized by what is stated in the independent claims. The preferred embodiments of the disclosure are disclosed in the dependent claims.

Detection of indicators of PD may be implemented with an electrode patch and a detection system and method according to the present disclosure.

The electrode patch may be in the form of a self-adhesive, patch or strip into which EMG electrodes have been embedded to a fixed configuration. The electrode patch may have flexible or rigid body, for example. Since the electrodes are in a fixed configuration, their distances and positioning with respect to each other always remain constant. This ensures consistent measurements results, thereby reducing the number of variables.

A detection system and method according to the present disclosure may be used to detect different indicators of PD in the measurement data. A principal component representation may be formed from the EMG and acceleration data. Principal components of the principal component representation may be selected such that it groups the measurement data into meaningful categories representing different indicators of type and/or stage and/or severity of symptoms or treatment response of PD. Magnitudes of the different indicators of PD in the measurement data can be calculated, and an assessment of the condition of the person can be formed on the basis of these magnitudes.

An electrode patch and a detection system according to the present disclosure provide a reliable, computationally cost-efficient tool for providing information that can be used in detecting indicators of PD in a person, in assessing progress of PD in the person, and in determining the efficiency of a treatment/medication for PD in the person.

The method and the electrode patch allow the person to move freely during a measurement period. Thus, the method and electrode patch enable measurement periods that may last several days instead of minutes or few hours. The ability to monitor and analyse continuous measurement data over longer periods of time can have a significant effect on forming a clear view on the symptoms and planning of optimal therapy with regards to drug type, and its dosage, and the dosage scheduling. Continuous and longer monitoring of data may also help in adjusting deep brain stimulation settings, and choosing optimal treatment method in each situation.

BRIEF DESCRIPTION OF THE DRAWINGS

In the following the invention will be described in greater detail by means of preferred embodiments with reference to the attached drawings, in which.

DETAILED DISCLOSURE

Figure 1:
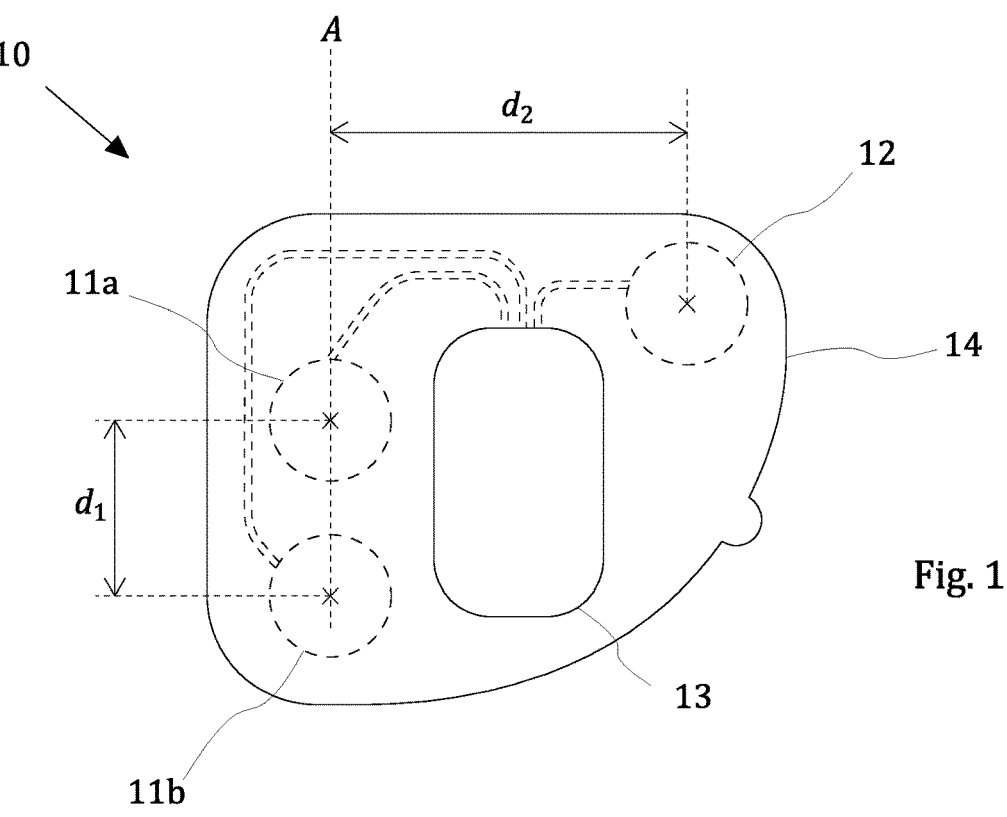
FIG. 1 shows an exemplary embodiment of an electrode patch according to the present disclosure.

The present disclosure describes a flexible or rigid electrode patch and a detection system/method for detecting an indicator of PD in a person. The at least one indicator may be detected in biosignal data, such as EMG and acceleration signal data, of the person. In the context of the present disclosure, biosignal data may represent samples of a biosignal or biosignals measured from the person, for example.

An electrode patch according to the present disclosure may comprise electrodes positioned for measuring the EMG signal from a muscle in upper or lower limb of the person. The positioning of the electrodes may be such that when a detection system according to the present disclosure receives the EMG signal, the detection system is able to detect an indicator of PD in a person. The acceleration signal data may represent samples of measurements measuring motion of a limb of a person. The acceleration data may originate from an acceleration sensor attached to the limb of the person. The type and configuration (sample rate, operating range) of the acceleration sensor may be selected for measuring acceleration data associated muscle activity, and in particular with PD, e.g. tremors.

The detection system may be configured to receive an EMG signal originating from the electrode patch that has been attached to upper or lower limb of the person and an acceleration signal associated with the EMG signal, determine a principal component representation of the EMG signal and the acceleration signal, and determine a magnitude of at least one indicator of PD based on the value of the principal component representation. The condition of the person may then be interpreted on the basis of the determined magnitude of the at least one indicator.

In the context of the present disclosure, the principal component representation is formed by one or more principal components. The principal component representation represents a projection of original signal features that may have correlations between each other into uncorrelated signal features in a feature space formed by orthogonal basis vectors. These uncorrelated signal features are the principal components. In the context of the present disclosure, the principal component representation may be based on at least one feature of the EMG signal and the acceleration signal, for example.

Various features of measurement data (i.e. samples of the EMG signal and the acceleration signal) may be utilized in determining the magnitude of the at least one indicator of PD. These features include statistical features of the signals, such as sample histograms, kurtosis and crossing rate, and spectral-based features, such as Fourier transform, periodogram and wavelets. Further, said features may include parameters based on nonlinear dynamics and interrelation between the EMG and the acceleration data, such as coherence and different types of cross-entropies.

A novel electrode patch according to the present disclosure may be used for the measurement of the EMG. The electrode patch may be disposable or reusable. The electrode patch may be made of a sheet of plastic and/or textile into which electrodes have been embedded, for example. Electrode patch may be flexible or rigid. Electrodes may be wet or dry. The measuring area of the electrodes may be circular or other shaped. The electrodes are preferably arranged to a specific configuration in order to ensure sufficient information content of the EMG signal.

Literature widely recommend using a centre-to-centre distance of 2 cm (0.75 inch) between the measurement electrodes in EMG measurements (see e.g. Hermens H J, Freriks B, Merletti R, Stegeman D, Blok J, Rau G, Disselhorst-Klug C, and Hägg G: European recommendations for surface electromyography. Roessingh Research and Development, ISBN 90-75452-15-2, 1999). However, in order to facilitate receiving electromagnetic signals from deeper inside below skin, a distance wider than the recommended 2 cm may be used in the electrode patch according to the present disclosure. Two measurement electrodes may be positioned parallel to the muscle fibres at a centre-to-centre distance of more than 2 cm to less than 4 cm, for example. A reference electrode may be positioned such that a distance from a centre of the reference electrode to an axis passing through centres of the measurement electrodes is at least the distance between the measurement electrodes. Preferably, the distance between the centres of the measurement electrodes is 2.5-3 cm. Reference electrode is preferably placed on an inactive area with regards to muscles. When this configuration of electrodes is being used together with the detection method/system according to the present disclosure, information content of the EMG signal data can be maximized.

A novel detection system and method according to the present disclosure may be used for the EMG signal data in order to determine the magnitude of the at least one indicator of PD on the basis of the measurement data. The EMG signal data preferably originates from an electrode patch according to the present disclosure. In the system and method, a principal component representation may be formed from the EMG signal data and acceleration signal data associated with the EMG signal data, for example. Features extracted from the measurement data of may be used to form a feature vector. Each feature vector may represent features of measurements of one person, for example.

In order to eliminate possible correlations between the extracted features in the feature vector, the feature vector may then be modelled as a weighted sum of basis vectors, where the basis vectors may have been previously solved as eigenvectors of a sample correlation matrix. The sample correlation matrix may have been formed on the basis of measurement data from a plurality of persons, for example. Principal components representing weights for the weighted sum may be solved for the feature vector as a least squares solution, for example.

The principal components are new, uncorrelated features that represent the measurement data in a feature space formed by the basis vectors. Together, the principal components form a principal component representation. However, in order to reduce complexity of the data, only the most significant features may be selected, and an approximation of the measurement data in a reduced-dimension feature space. For example, the principal components may be selected such that measurement data from persons with PD (or a specific type of PD) cluster together in the feature space. Further, the principal components may also be selected such that the data forms clusters representing different severity/stage of PD or effectiveness of particular treatments, for example. Based on the clusters, simple rules for categorizing measurement results can be formed. Once the rules have been determined, measurement can be reliably categorized by applying the rules to a principal component representation of the EMG and acceleration data.

A measurement arrangement implementing the detection system and method according to the present disclosure may be implemented in various ways. For example, a measurement arrangement for detecting an indicator of PD in a person may comprise a flexible or rigid electrode patch according to the present disclosure, a (wearable) sensor module connected to the electrodes of the electrode patch, and a detection system according to the present disclosure. The sensor module may comprise means for measuring an EMG signal from the electrodes, means for measuring an acceleration signal from the upper or lower limb of the person, and means for transmitting the EMG signal and the acceleration signal to the detection system, for example. A computer, cluster of computer servers, or a computing cloud may be used to implement the detection system/method according to the present disclosure. The detection system may receive the measurement data directly from the sensor module or the measurement data may be relayed via transceiver unit. The transceiver unit may be a wireless communications unit, such as a wireless internet router, for example. A smart phone, tablet computer or other portable computing device with wireless communications capabilities may also be used a transceiver unit.

FIG. 1 shows an exemplary embodiment of an electrode patch according to the present disclosure. In FIG. 1, a diagrammatic view of a top side of a self-adhesive electrode patch 10 is shown. The body 14 of the electrode patch may be made of a flexible material, such as plastics of textile or their combination. The electrode patch 10 comprises two measurement electrodes 11a and 11b, and a reference electrode 12 attached or embedded to the body 14 such that surfaces of the electrodes are exposed on the bottom side of the electrode and form a galvanic connection to the skin of person when the patch is applied. In FIG. 1, the measurement electrodes have essentially circular shapes. The sensing area of the electrode can also be rectangular-shaped if this is more suitable for the manufacturing process. The centres of the measurement electrodes 11a and 11b are positioned at a distance $d_1$ from each other. The distance $d_1$ is 3 cm in FIG. 1. The reference electrode 12 is positioned aside of the measurement electrodes (i.e. laterally displaced at a distance $d_2$ from an axis A passing through the centres of the measurement electrodes 11a and 11b). The distance $d_2$ may be at least the distance $d_1$, preferably at least twice the distance $d_1$.

The body 14 of the electrode patch 10 may have a self-adhesive surface on its bottom side and a water resistant coating on its top side. The patch 10 in FIG. 1 may be provided with elongated openings that allow the skin below the patch to breathe. The top side of the patch 10 may have guide markings that help in positioning the patch correctly. The electrode patch may comprise a peel pad on its side in order to facilitate easy removal of the patch once the measurement has been finished.

FIG. 1 also shows a measurement unit 13 on the top side of the electrode patch. The measurement unit is galvanically connected to the electrodes 11a, 11b, and 12 by flexible conducting wires. The measurement unit 13 may be integrated to the electrode patch 10 or it may be detachably connected. For example, the patch 10 may comprise a connector interface in order to form a galvanic connection between the electrodes 11a, 11b, and 12 and a small, wearable measurement unit 13 measuring the EMG of the person. The portable measurement unit 13 may also comprise acceleration sensor for providing the acceleration data used in the method. The measurement unit 13 may be battery-powered and may be detachably attached to the electrode patch 10 via the connector interface 13. The electrode patch may comprise a dock, a pocket or a pouch into which the measurement unit may be placed during use.

Figure 2:
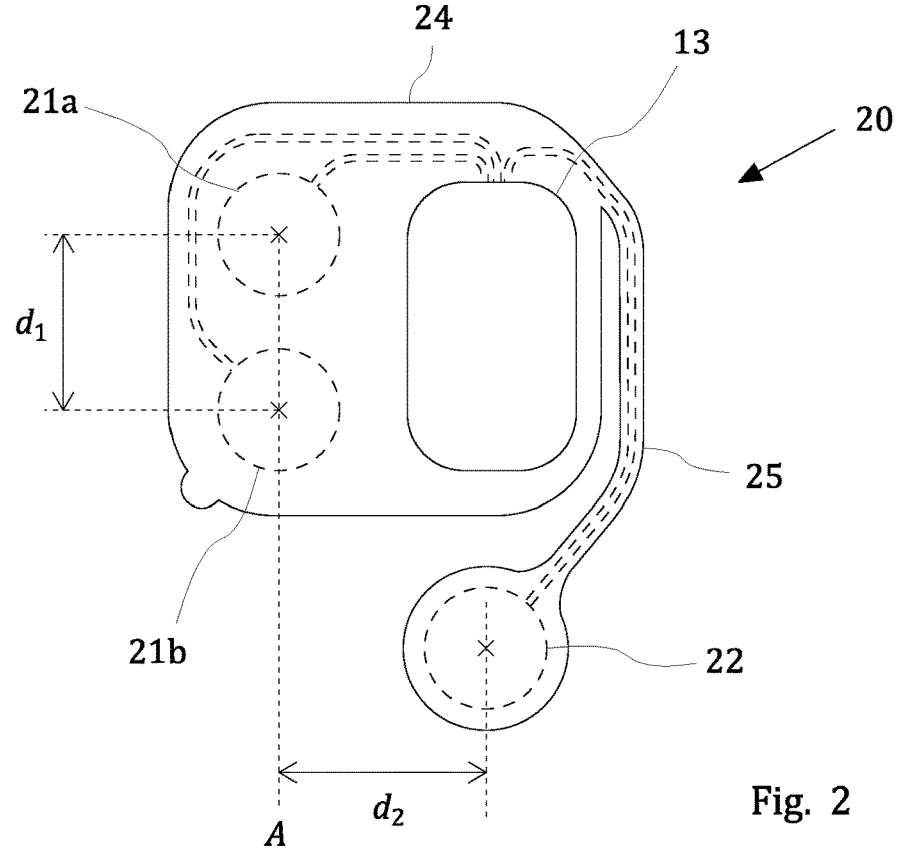
FIG. 2 another example of an electrode patch according to the present disclosure.

FIG. 2 shows another example of an electrode patch according to the present disclosure. The details of the patch 20 are similar in most parts with the patch 10 in FIG. 1. However, a conducting wire forming a connection between the measurement unit 13 and a reference electrode 22 is arranged on the end of a thin, elongated, and flexible strip 25. Said strip 25 extends from the body 24 of the electrode patch 20. This allows adjustment of the position of the reference electrode 22 with respect to the measuring electrodes 21a and 21b of the electrode patch 20, which may be useful with persons with very large diameter of the limb.

Figure 3:
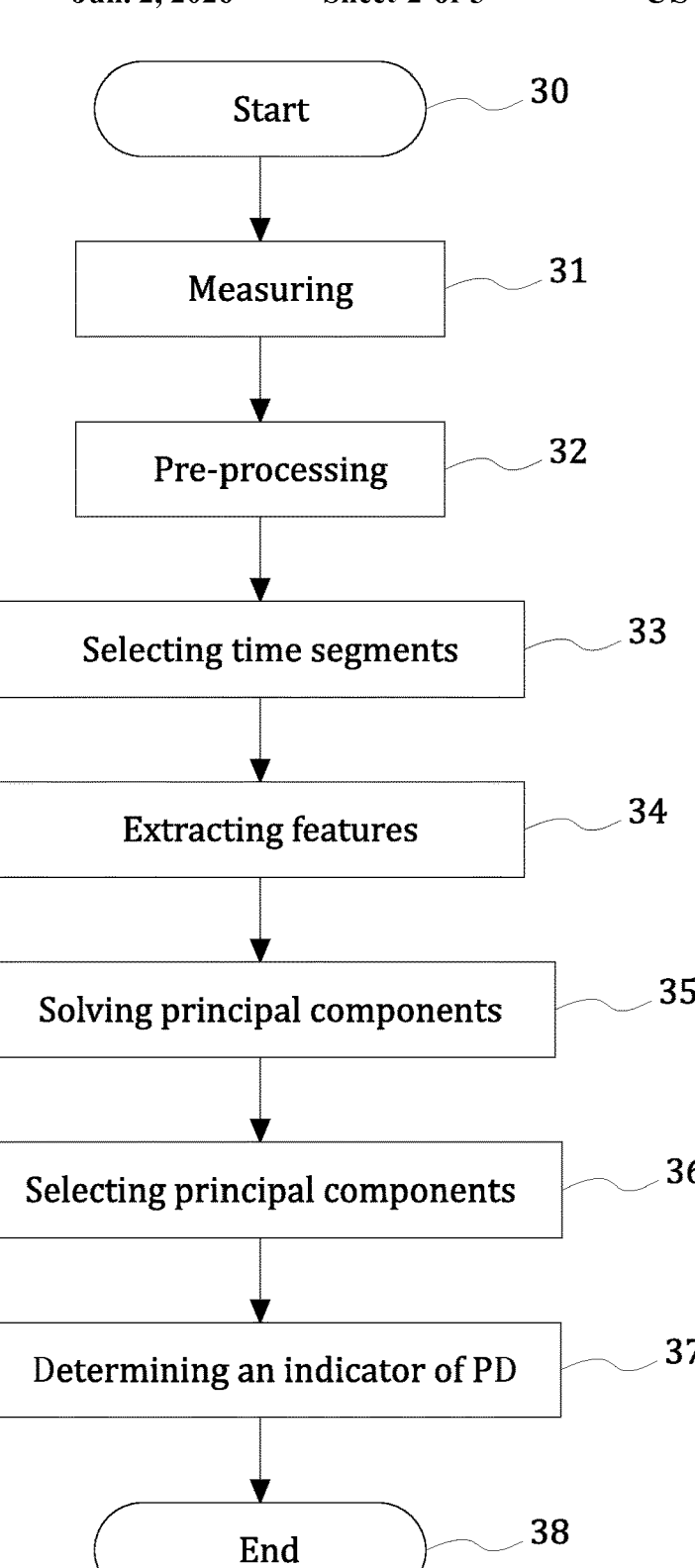
FIG. 3 shows an exemplary, simplified flow diagram of determining suitable indicators.

FIG. 3 shows an exemplary, simplified flow diagram of determining suitable indicators. In FIG. 3, the procedure comprises an initial step 30, follows through consecutive steps 31-37, and finally ends at end step 38.

The procedure starts at step 30 from which the procedure continues to step 31. In step 31, raw EMG signals are band-pass filtered, amplified and A/D converted. The band-pass filter may be an analog anti-aliasing filter (Butterworth, band-pass 1-500 Hz), and the A/D conversion may be made with a 14-bit A/D converter, for example. Further, motion of limb is registered by using an accelerometer, e.g. a tri-axial accelerometer (range ±16 g, 14-bit A/D converter).

Next, in step 32, EMG- and acceleration signals are pre-processed. Possible noise may be removed from measured EMG data by using low-pass or band-pass and/or notch filtering, for example. The noise may be originated from surrounding electrical devices (e.g. a DBS unit) and motion, for example.

In the subsequent step 33, representative time segments of data are be selected for analysis. Preferably, these segments include muscle activities measured during static and dynamic contractions. In addition, these segments preferably cover different times of day (morning, afternoon, evening and night).

Next, in step 34, several features are extracted from the EMG and acceleration signals. These features may include at least a sample histogram, parameters describing EMG morphology (e.g. sample kurtosis and crossing rate variable) and parameters based on nonlinear dynamics (e.g. recurrence rate of the EMG signal and sample entropy of the acceleration signal), for example.

In the subsequent step 35, extracted EMG and acceleration signal features are used to form a feature vector. Each feature vector may then be modelled as a weighted sum of basis vectors, where the basis vectors may have been previously solved as eigenvectors of a sample correlation matrix. The sample correlation matrix may be formed on the basis of gathered person data, for example. The weights (principal components) may be solved for each feature vector of a person as a least squares solution, for example.

In the next step 36, the solved principal components are used to identify changes in the neuromuscular and motor function of subjects between different times of day, between different DBS settings, or between different treatment methods, for example. Only the most significant principal components with regards to symptom severity, treatment response and type of PD may be chosen for further analysis.

Next, in step 37, the high-dimensional features formed in step 35 are projected to lower-dimensional space using the chosen principal components. The chosen principal components are used for calculation of indicator that presents the clinical condition of person. The calculated indicator may be time varying scalar value and it may be presented as a graph, for example. The indicator may also be of higher dimension such as a point in two-dimensional plane, for example. The procedure then ends at step 38.

Figure 4:
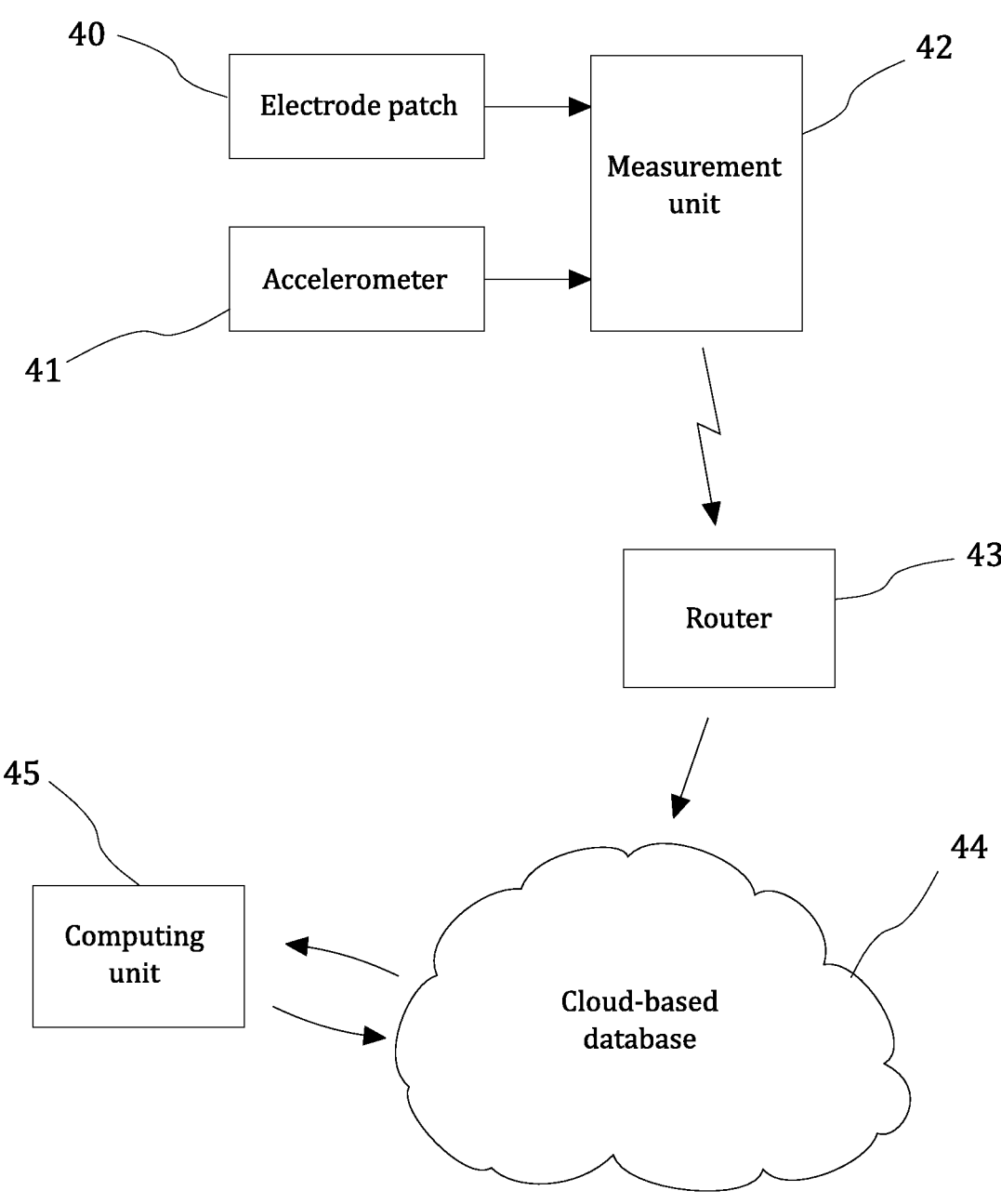
FIG. 4 shows an example of a measurement arrangement according to the present disclosure.

FIG. 4 shows an example of a measurement arrangement according to the present disclosure. In FIG. 4, electrical activation of a muscle is registered (in the form of an EMG signal) by using an electrode patch 40 according to the present disclosure. The electrode patch 40 may be the same as or similar to the examples of FIGS. 1 and 2, for example. In addition, limb motion is simultaneously registered in FIG. 4 by using an accelerometer 41. In some embodiments, the accelerometer 41 may be integrated to the measurement unit. Alternatively, the accelerometer may be a separate unit.

In FIG. 4, the electrode patch 40 and the accelerometer 41 provide an EMG signal and an acceleration signal (e.g. in the form of analog voltage signals) to a measurement unit 42 where the signals may be A/D converted. The A/D-converted signal data may be either saved into a memory card of the measurement unit 42 (i.e. off-line mode), or sent to a router device 42 (i.e. online mode) that may be a computer or a smart device, for example. In the offline mode, after a measurement session has ended, the measurement data may be uploaded from the memory card to the router device 43. In the online mode, the measurement unit may send some or all signal data to the router device already before the end of a measurement session. Preferably, the communication between the measurement unit 42 and the router 43 is wireless as this allows the person to move more freely. The router device 43 may be a wireless communications unit, such as a wireless internet router, for example. A smart phone, tablet computer or other portable computing device with wireless communications capabilities may also be used as the router device 43.

The signal data provided by the measurement unit 42 to the router device 43 may be a raw A/D-converted signal data or it may be preprocessed by the measurement unit 42. For example, the measurement unit may be configured to perform one or both of steps 32 and 33 in the embodiment of FIG. 3. The measurement unit 42 in FIG. 4 may support both the offline mode and the online mode, and a user may select which of the two modes to use.

In FIG. 4, the signal data is forward to a cloud-based database 44 from the router device 43. From the cloud-based database 44, the signal data is sent to a computing unit 45 that may be a computer or server containing an analysis program, for example. The analysis program which may be in the form of a software program may be configured to carry out a method according to the present disclosure. Thus, the analysis program may be configured for detecting an indicator of PD in the person. The analysis program may be configured to receive (e.g. from the cloud-based database 44) an EMG signal originating from an electrode patch attached to a limb of the person and an acceleration signal associated with the EMG signal, determine a principal component representation of the EMG signal and the acceleration signal, wherein the principal component representation represents a projection of at least one feature of the EMG signal and the acceleration signal into a feature space formed by orthogonal basis vectors, and determine a magnitude of the indicator of PD based on the principal component representation. For example, the analysis program may implement the steps 34 to 37 of the example of FIG. 3 in order to detect an indicator of Parkinson's disease.

Once the analysis program in computing unit 45 has been executed, the analysis results may be sent from the computing unit 45 back to the cloud-based database 44, from where they can be accessed by the doctor who is either in charge of the person's treatment or asked to give his/her statement on results, for example.

The above discussed measurement system may be used as follows, for example.

First, the skin of the person over a muscle of interest is preferably shaved (if required) and rubbed with alcohol. An electrode patch according to the present disclosure may then be placed on the skin and according to the present disclosure may be attached to the electrode patch. A person in charge of the measurement session may check the quality of EMG signals, and start a continuous measurement of EMG and motion which may last for several days, for example. During the measurement, the person is free to move and do his/her daily activities.

The system collects EMG- and motion-based data and either saves them to the measurement unit or transfers it to a cloud-based database. The measured data is then analyzed, and the analysis results are provided to a doctor, who is in charge of the person's treatment. The doctor makes the decision on whether or not to use the results as help in doing the diagnosis or adjusting treatment.

The measurement and analysis according to the present disclosure may be performed for Parkinson patients with DBS therapy, for example. The analysis results may be used as help for adjusting the DBS settings. By performing the measurement before and after the adjustment of DBS settings, the outcome of DBS setting changes can be evaluated. By performing the measurement before and after DBS surgery, the outcome of DBS surgery can be evaluated.

The measurement and analysis according to the present disclosure may also be performed for Parkinson patients with drug therapy. Analysis results describing the time-varying symptoms may be used as an aid for adjusting the drug therapy such as for choosing optimal drug types, for adjusting drug dosages, and for scheduling of drug doses. The analysis results may also be used as help in screening the need for other type of therapy such as the need for DBS therapy.

The measurement and analysis according to the present disclosure may also be performed for Parkinson patients that participate in a clinical trial of drug development. Analysis results may help the drug developers in comparing different drugs and/or evaluating drug efficacy.

The measurement and analysis according to the present disclosure may also be performed for during a surgical operation such as an implantation of neurostimulation system. The measurement system may collect EMG- and motion-based signals continuously and send them to a routing device such as a personal computer or smart device. The measurement data and analysis results are shown online on the personal computer or smart device. The doctor may use the measurement data and analysis results as help for adjusting stimulation electrode placement, configurations and stimulation settings during surgery.

It is obvious to a person skilled in the art that the electrode patch and the detection method/system can be implemented in various ways. The invention and its embodiments are not limited to the examples described above but may vary within the scope of the claims.

The invention claimed is:

1. A measurement arrangement for generating an indicator of Parkinson's disease in a person, wherein the measurement arrangement is suitable for prolonged, continuous measurements, and wherein the measurement arrangement comprises:

a surface electrode patch configured to simultaneously measure an electromyography (EMG) signal from a muscle in a single limb of the person and measure an acceleration signal associated with muscle activities of the limb, the surface electrode patch comprising:

EMG measurement electrodes configured to be positioned parallel to muscle fibers of the limb, a reference electrode configured to be placed on an inactive muscle area of the limb, an acceleration sensor configured to be attached to the limb, for generating the acceleration signal, and a measurement unit connected to the EMG measurement electrodes, the reference electrode, and the acceleration sensor, the measurement unit comprising:

an analog to digital converter for converting the EMG signal and the acceleration signal, a memory for saving the converted EMG and acceleration signals in an offline mode, and a wireless communication capability for sending the converted EMG and acceleration signals in an online mode, a computing unit configured to:

receive the converted EMG and acceleration signals, determine principal component representations based on the received converted EMG and acceleration signals, wherein each principal component representation represents a projection of at least one feature of the received converted EMG signal and at least one feature of the received converted acceleration signal into uncorrelated features in a feature space formed by orthogonal basis vectors, for each determined principal component representation, determine a magnitude of the indicator based on the respective principal component representation, and based on the determined magnitudes based on the respective principal component representations, provide the indicator of Parkinson's disease as a time varying scalar value that shows changes of the magnitudes of the indicator of Parkinson's disease over time, wherein determining each principal component representation comprises:

selecting time segments of the converted EMG and acceleration signals related to muscle activities during static and dynamic contractions;

extracting the at least one feature of the received converted EMG signal from the selected time segments of the converted EMG signal and extracting the at least one feature of the received converted acceleration signal from the selected time segments of the received converted acceleration signal, forming a feature vector based on the extracted features, wherein the feature vector is represented as a weighted sum of eigenvectors of a sample correlation matrix, the sample correlation matrix being previously determined based on measurement data of a plurality of persons, solving weights for the weighted sum, and using the weights as principal components of the respective principal component representation.

2. The measurement arrangement according to claim 1, wherein:

the at least one feature extracted from the EMG signal comprises at least parameters describing EMG morphology and a recurrence rate of the EMG signal, and the at least one feature extracted from the acceleration signal comprises a sample entropy of the acceleration signal.

3. The measurement arrangement according to claim 2, wherein the computing unit is further configured to present the indicator on a display in a form of a graph showing the changes of the magnitude of the indicator over time.

4. The measurement arrangement according to claim 1, wherein a distance between centres of the measurement electrodes is above 2 cm and less than 4 cm, and that the reference electrode is adapted to be positioned such that a distance from a centre of the reference electrode to an axis passing through the centres of the measurement electrodes is at least the distance between the centres of the measurement electrodes during use.

5. The measurement arrangement according to claim 4, wherein the distance between the centres of the measurement electrodes is 2.5 cm-3 cm.

6. The measurement arrangement according to claim 4, wherein the reference electrode is adapted to be positioned such that the distance from the centre of the reference electrode to the axis passing through the centres of the measurement electrodes is at a fixed lateral distance of 4-8 cm.

7. The measurement arrangement according to claim 4, wherein the electrode patch comprises an elongated, flexible strip at an end of which the reference electrode has been positioned so that the distance from the centre of the reference electrode to the axis passing through the centres of the measurement electrodes can be adjusted when applying the electrode patch to skin of the person.

8. The measurement arrangement according to claim 1, wherein the wireless communication capability comprises:

a transceiver unit for sending the converted EMG signal and the converted acceleration signal to the computing unit.

9. The measurement arrangement according to claim 1, wherein the computing unit is further configured to present the indicator on a display in a form of a graph showing the changes of the magnitude of the indicator over time.

10. A computer implemented method for continuously monitoring an indicator of symptoms of Parkinson's disease (PD) in a person, wherein the method is suitable for prolonged measurements and comprises:

continuously receiving signals originating from a surface electrode patch configured to simultaneously measure an electromyography (EMG) signal from a muscle in a single limb of the person and an acceleration signal associated with muscle activity of the limb, the surface electrode patch comprising:

EMG measurement electrodes configured to be positioned parallel to muscle fibers of the limb, a reference electrode configured to be placed on an inactive muscle area of the limb, an acceleration sensor configured to be attached to the limb, for generating the acceleration signal, and a measurement unit connected to the EMG measurement electrodes, the reference electrode, and the acceleration sensor, the measurement unit comprising:

an analog to digital converter for converting the EMG signal and the acceleration signal, a memory for saving the converted EMG and acceleration signals in an offline mode, and a wireless communication capability for sending the converted EMG and acceleration signals in an online mode, using a computing unit to:

receive the converted EMG signal and the converted acceleration signal, determine principal component representations based on the received converted EMG signal and the received converted acceleration signal, wherein each principal component representation represents a projection of at least one feature of the received converted EMG signal and at least one feature of the received converted acceleration signal into uncorrelated features in a feature space formed by orthogonal basis vectors, for each determined principal component representation, determine a magnitude of the indicator based on the respective principal component representation, and based on the determined magnitudes based on the respective principal component representations, provide the indicator of the symptoms of Parkinson's disease (PD) as a time varying scalar value that shows changes of the magnitudes of the indicator of the symptoms of Parkinson's disease (PD) over time, wherein determining each principal component representation comprises:

selecting time segments of the converted EMG and acceleration signals related to muscle activities during static and dynamic contractions;

extracting the at least one feature of the received converted EMG signal from the selected time segments of the converted EMG signal and at the the at least one feature of the received converted acceleration signal from the selected time segments of the received converted acceleration signal, forming a feature vector based on the extracted features, wherein the feature vector is represented as a weighted sum of eigenvectors of a sample correlation matrix, the sample correlation matrix being previously determined based on measurement data of a plurality of persons, solving weights for the weighted sum, and using the solved weights as principal components of the respective principal component representation.

11. The method according to claim 10, wherein the features extracted from the EMG signal and the acceleration signal comprise at least parameters describing EMG morphology, and a recurrence rate of the EMG signal, and a sample entropy of the acceleration signal.

12. The method according to claim 11, wherein the method further comprises presenting the indicator on a display in a form of a graph showing the changes of the magnitude of the indicator over time.

13. The method according to claim 10, wherein a distance between centres of the measurement electrodes is above 2 cm and less than 4 cm, and that the reference electrode is adapted to be positioned such that a distance from a centre of the reference electrode to an axis passing through the centres of the measurement electrodes is at least the distance between the centres of the measurement electrodes during use.

14. The method according to claim 13, wherein the distance between the centres of the measurement electrodes is 2.5 cm-3 cm.

15. The method according to claim 10, wherein the method further comprises presenting the indicator on a display in a form of a graph showing the changes of the magnitude of the indicator over time.

16. The method according to claim 10, wherein the wireless communication capability comprises a transceiver unit for sending the converted EMG signal and the converted acceleration signal to the computing unit.

\* \* \* \* \*